US006667397B2

(12) United States Patent
Debenham et al.

(10) Patent No.: US 6,667,397 B2
(45) Date of Patent: Dec. 23, 2003

(54) METHODS OF PREPARING DISACCHARIDE AND TRISACCHARIDE $C_6$-$C_{12}$ FATTY ACID ESTERS WITH HIGH ALPHA CONTENT AND MATERIALS THEREFROM

(75) Inventors: John Steele Debenham, Kingsport, TN (US); Charles Michael Buchanan, Kingsport, TN (US); Matthew Davie Wood, Gray, TN (US); Michael Orlando Malcolm, Kingsport, TN (US); Mary Kathleen Moore, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/933,409

(22) Filed: Aug. 20, 2001

(65) Prior Publication Data

US 2002/0103369 A1 Aug. 1, 2002

Related U.S. Application Data

(60) Provisional application No. 60/227,990, filed on Aug. 25, 2000.

(51) Int. Cl.$^7$ ................................................ C07H 13/06
(52) U.S. Cl. .................. 536/124; 536/1.11; 536/123.13
(58) Field of Search .............................. 536/55.1, 1.11, 536/119, 5, 6, 69, 115, 123.13, 124; 424/65, 66, 400, 401

(56) References Cited

U.S. PATENT DOCUMENTS

| | | | |
|---|---|---|---|
| 3,956,278 A | * 5/1976 | Prey | ........................ 536/119 |
| 4,980,463 A | * 12/1990 | Walkup et al. | .............. 536/124 |
| 5,294,703 A | 3/1994 | Hyatt et al. | |
| 6,083,492 A | 7/2000 | Modi | |
| 6,248,312 B1 | * 6/2001 | Franklin et al. | .............. 424/65 |
| 6,287,544 B1 | 9/2001 | Franklin et al. | |
| 2001/0033851 A1 | 10/2001 | Franklin et al. | |

FOREIGN PATENT DOCUMENTS

| | | | |
|---|---|---|---|
| JP | 10251286 | 9/1998 | |
| WO | WO 91/16356 | * 10/1991 | ............. C08B/3/02 |

OTHER PUBLICATIONS

Takada, A. et al "Discotic columnar liquid crystals in oligosaccharide derivatives III. Anomeric effects on the thermomesomorphic properties of cellobiose octa–alkanoates", Liquid Crystals, 1995, vol. 19, No. 4, pp 441–448.*

Amelung et al., "Determination of Neutral and Acidic Sugars in Soil by Capillary Gas–Liquid Chromatography after Trifluoroacetic Acid Hydrolysis," *Soil Biol. Biochem.,* 28(12):1631–1639 (1996).

Arakawa et al., "Determination of Neutral and Amino Sugars in Glycoproteins by Gas Chromatography," *Chem. Pharm. Bull.,* 24(9):2032–2037 (1976) (Abstract).

Collins et al., "Monosaccharides Their Chemistry and Their Roles in Natural Products," Wiley & Sons, 362–363 (1995).

Debenham et al., "Two New Orthogonal Amine–Protecting Groups That Can be Cleaved under Mild or Neutral Conditons," *J. Am. Chem. Soc.,* 117:3302–3303 (1995).

Fan et al., "Comparison of Acid Hydrolytic Conditions for Asn–Linked Oligosaccharides," *Anal. Biochem.,* 219(2):375–378 (1994) (Abstract).

Hamalainen et al., "Fibrous Cellulose Esters by Trifluoroacetic Anhydride Method," *Text. Research Jour.,* 27:168 (1957).

Hudson et al., "A Comparison of the Optical Rotatory Powers of the Alpha and Beta Forms of Certain Acetylated Derivatives of Glucose," *J. Am. Chem . Soc.,* 37:1264–1270 (1915).

Morooka et al., "Dielectric Properties of Cellulose Acylates," *J. Appl. Polym. Sci.,* 29:3981–3990 (1984).

Takada et al., "Discotic Columnar Liquid Crystals in Oligosaccharide Derivatives III. Anomeric Effects on the Thermo–Mesomorphic Properties of Cellobiose Octa–alkanoates," *Liquid Crystals,* 19(4): 441–448 (1995).

Takada et al., "Chain–Length Dependence of the Mesomorphic Properties of Fully Decanoated Cellulose and Cellooligosaccharides," *Macromolecules,* 27:1651–1653 (1994).

Takada et al., "Columnar Liquid Crystals in Oligosaccharide Derivatives II. Two Types of Discotic Columnar Liquid–Crystalline Phase of Cellobiose Alkanoates," *Liquid Crystals,* 12(2):337–345 (1992).

Takada et al., "Columnar Liquid Crystals in Oligosaccharide Derivatives I. Discotic Columnar Liquid Crystals in Cellobiose Octadecanoate and Cellotriose Hendecadecanoate," *Liquid Crystals,* 9(2):221–228 (1991).

Takada et al., "Preparation of Cellobiose Octa(n–alkanoate)s and Their Thermal Properties," *Bull. Inst. Chem. Res.,* 69(2):77–83 (1991).

* cited by examiner

Primary Examiner—James O. Wilson
Assistant Examiner—Ganapathy Krishnan
(74) Attorney, Agent, or Firm—Bernard J. Graves; Michael J. Blake

(57) ABSTRACT

The present invention provides chemical processes for the preparation of disaccharide and trisaccharide $C_6$ to $C_{12}$ fatty acid esters having a high alpha content. Yet still further, the invention provides materials prepared by the processes disclosed herein.

22 Claims, 6 Drawing Sheets

FIG.2 THE CHEMICAL CONVERSION OF β-D-CELLOBIOSE TO α-D-CELLOBIOSE OCTANONANOATE.

α-CONTENT vs. VOLUMES OF PRECIPITATION SOLUTION.

METHODS OF PREPARING DISACCHARIDE AND TRISACCHARIDE $C_6$-$C_{12}$ FATTY ACID ESTERS WITH HIGH ALPHA CONTENT AND MATERIALS THEREFROM

CROSS-REFERENCE TO RELATED APPLICATIONS

This application claims priority to U.S. Provisional Application No. 60/227,990 filed Aug. 25, 2000, which application is incorporated in its entirety by this reference.

FIELD OF THE INVENTION

This invention relates to novel processes for preparing disaccharide or trisaccharide $C_6$–$C_{12}$ fatty acid esters having high i-content and materials prepared therefrom. The invention also relates to processes for preparing high a-content cellobiose $C_6$–$C_2$ fatty acid esters and materials prepared therefrom.

BACKGROUND OF THE INVENTION

Highly substituted fatty acid esters of disaccharide and trisaccharides are useful materials. These materials can form discotic columnar liquid crystals. They may also serve as thickeners, plasticizers, and rheology modifiers.

Cellobiose alkanoates have unique physical properties. It is known that the α-anomer form of the cellobiose ester generally forms more stable mesophases than does the β-anomer. Takada and coworkers describe the preparation of high a-content cellobiose octanonanoate ("CBON"). (Takada, A.; Ide, N.; Fukuda, T.; Miyamoto, T. *Liq. Crystals* 1995, 19, 441–448). This paper describes in limited detail a method to produce both high alpha content and high beta content cellobiose octanonanoate and other fatty acid esters.

There has not been described an efficient process to prepare cellobiose fatty acid esters having a high a-content. A primary drawback in the prior art methods is the need for extensive processing of the product to obtain sufficiently high purity of the disaccaharide and trisaccharide fatty acid esters directly from the esterification reaction. Those skilled in the art would recognize that further enrichments in the purity of the product (alpha content) can be obtained by additional recrystallization through any number of standard methods. One of skill in the art will recognize that repeated recrystallization can add considerable expense to the production and can greatly reduce the product yield, thus making the process impractical for an industrial scale. Therefore, it would be highly desirable to develop a process to prepare high purity disaccharide and monosaccharide fatty acid esters wherein such materials may be utilized as prepared from an esterification reaction without the need for purification. Moreover, it would be highly desirable to develop processes wherein novel disaccharide and trisaccharide fatty acid esters are prepared.

BRIEF SUMMARY OF THE INVENTION

This invention relates to novel processes for preparing disaccharide or trisaccharide $C_6$–$C_{12}$ fatty acid esters having a high α-content and materials prepared therefrom. The invention also relates to processes for preparing high α-content cellobiose $C_6$–$C_{12}$ fatty acid esters and materials prepared therefrom.

Additional advantages of the invention will be set forth in part in the detailed description, which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory aspects of the invention, and are not restrictive of the invention, as claimed.

DETAILED DESCRIPTION OF THE INVENTION

Figure 1:
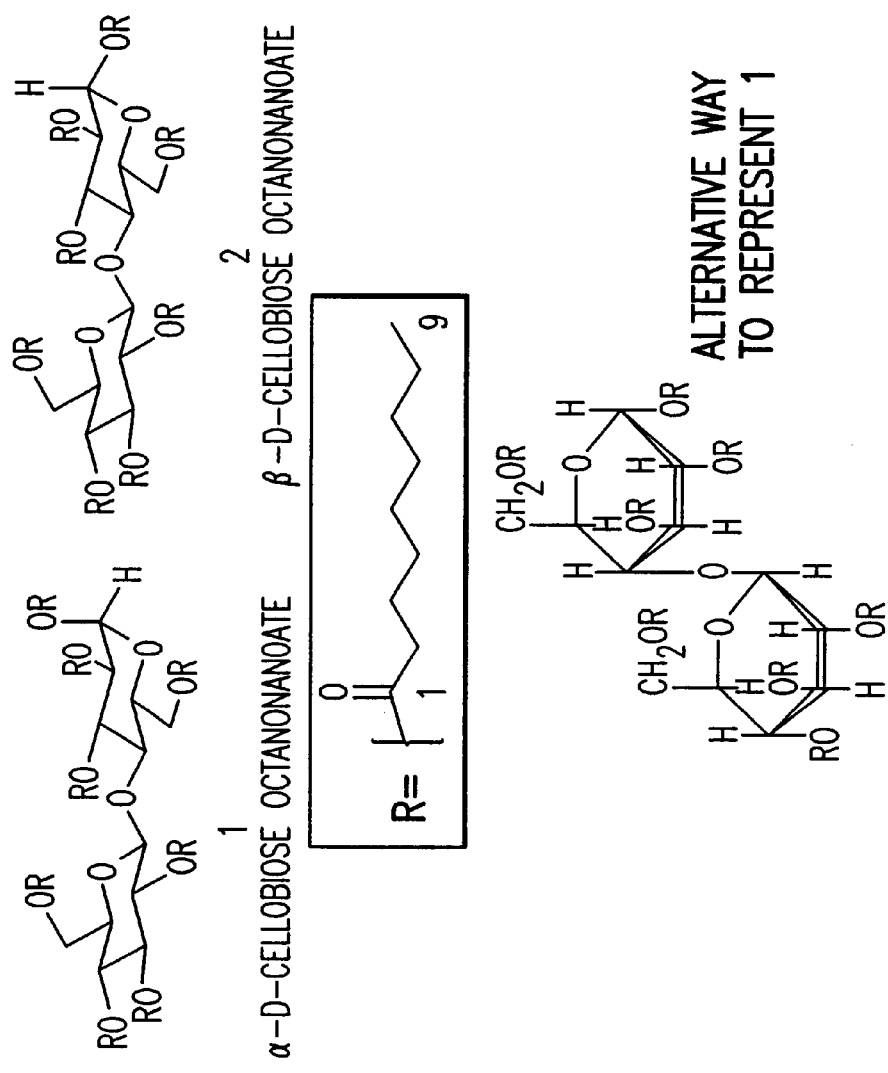
FIG. 1 provides the chemical structures of α and β-cellobiose octanonanoate.

The present invention provides chemical processes for the preparation of disaccharide and trisaccharide $C_6$ to $C_{12}$ fatty acid esters having high alpha content.

Yet still further, the invention provides materials prepared by the processes disclosed herein.

The present invention may be understood more readily by reference to the following detailed description of the invention and the examples provided therein. It is to be understood that this invention is not limited to the specific methods, formulations, and conditions described, as such may, of course, vary. It is also to be understood that the terminology used herein is for the purpose of describing particular aspects only and is not intended to be limiting.

In this specification and in the claims that follow, reference will be made to a number of terms, which shall be defined to have the following meanings.

The singular forms "a," "an," and "the" include plural referents unless the context clearly dictates otherwise.

Ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

Throughout this application, where patents are referenced, the disclosures of these patents in their entireties are hereby incorporated by reference into this application in order to more fully describe the state of the art to which this invention pertains.

In a first major aspect, the invention provides a method for preparing a disaccharide or a trisaccharide $C_6$–$C_{12}$ fatty acid ester comprising the steps of: a) combining a disaccharide or a trisaccharide-containing material, a $C_6$–$C_{12}$ fatty acid anhydride-containing material and a catalyst to provide a reaction mixture; and b) contacting the reaction mixture for a time and at a temperature sufficient to provide a dissacharide or trisaccharide $C_6$–$C_{12}$ fatty acid ester with an α-content of from greater than about 50% to about 100%. In a further aspect, the α-content of the disaccharide or trisaccharide $C_6$–$C_{12}$ fatty acid ester is from about 75 to about 100%. The α-content may be at least about 75% or, still further, from about 75% to about 100%. Still further, the α-content may be from about 55% to about 60% or about 70%, or about 75%, or about 80%, or about 85%, or about 90%, or about 95%, where any upper value may be used with any lower value.

Disaccharide and trisaccharide containing materials suitable for use in the present invention include but are not limited to: cellobiose, cellotriose, maltose, lactose, and other disaccharide and trisaccharides of hexose sugars. Anhydride containing materials include but are not limited to: hexanoic anhydride, heptanoic anhydride, octanoic anhydride, nonanoic anhydride, decanoic anhydride, undecanoic anhydride and dodecanoic anhydride mixtures thereof, along with the corresponding carboxylic acids, and mixtures thereof.

In a further aspect, the disaccharide or trisaccharide-containing material comprises cellobiose, thereby providing a cellobiose $C_6$ to C12 ester. As utilized herein, "cellobiose" means 4-O-β-D-glucopyranosyl-D-glucose. Cellobiose suitable for use in the invention may be derived from any source including, but not limited to, the enzymatic digestion of cellulose to cellobiose or the chemical deacetylation of cellobiose octaacetate. Cellobiose may be obtained, for example, from CMS Chemicals (Oxfordshire, UK). Cellobiose may also be obtained by obtaining by subjecting alpha-D-cellobiose octaacetate to a methanolysis step. One method of preparing alpha-D-cellobiose octaacetate is disclosed in U.S. Pat. No. 5,294,793, which disclosure is incorporated herein in its entirety by this reference.

The cellobiose $C_6$–$C_{12}$ fatty acid esters of the present invention may comprise a cellobiose $C_8$–$C_{10}$ ester with an α-content greater than about 50% to about 100% or, still further, the α-content may be from about 75% to about 100%. In a particular aspect, the cellobiose fatty acid ester comprises a cellobiose octanonanoate with an α-content of greater than about 50%, or, still further, the α-content may be at least about 75% or, still further, from about 75% to about 100%. Still further, the α-content may be from about 55% to about 60% or about 70%, or about 75%, or about 80%, or about 85%, or about 90%, or about 95%, where any upper value may be used with any lower value.

In yet a further aspect, the disaccharide or trisaccharide $C_6$–$C_{12}$ fatty acid ester, whether or not comprising a cellobiose fatty acid ester, may be subjected to a purification or a recrystallization step after step (b), thereby increasing the α-content of the disaccharide or trisaccharide $C_6$ to $C_{12}$ ester.

It has been found in accordance with the methods herein that additional anomerization of the disaccharide and trisaccharide $C_6$–$C_{12}$ fatty acid esters can occur following step (b) if the reaction mixture contains residual catalyst, fatty acid and/or anhydride-containing material comprising $C_6$–$C_{12}$ fatty acid anhydride and/or $C_6$–$C_{12}$ fatty acid. For example, when the anhydride-containing material comprises nonanoic anhydride, thereby providing a cellobiose octanonanoate, a range of residual reactants could be from about 500 to about 3000 ppm catalyst and from about 5 to about 25% nonanoic acid, nonanoic anhydride or a mixture thereof. A particular final α-content of the disaccharide or trisaccharide $C_6$ to $C_{12}$ fatty acid ester maybe from about 85 to about 95% for this post reaction anomerization process. Thus, in accordance with the methods and compositions herein, the disaccharide or trisaccharide $C_6$–$C_{12}$ fatty acid ester, whether or not purified or recrystallized from the reaction mixture, may be treated at from about 20° C. to about 60° C. in the presence of sufficient reactant (catalyst, anhydride and/or fatty acid ester) after step (b), thereby further increasing the α-content of the disaccharide or trisaccharide $C_6$ to $C_{12}$ fatty acid ester while minimizing further glycosidic cleavage and byproduct formation. One of ordinary skill in the art will recognize that, in one aspect, glycosidic cleavage and by-product formation be minimized so as to enhance the useful properties of the materials prepared herein.

With respect to the esterification/anomerization of the disaccharide or trisaccharide $C_6$–$C_{12}$ fatty acid esters herein, the materials comprising the reaction mixture (disaccharide or trisaccharide-containing material) may be contacted at a temperature of from about 40° C. to about 110° C., or, still further, from about 70° C. to about 100° C.

Those of ordinary skill in the art will recognize that the temperature of the reaction, equivalents of anhydride and amount of catalyst used may influence the time required for esterification and speed of anomerization e.g., degree and amount.

Figure 2:
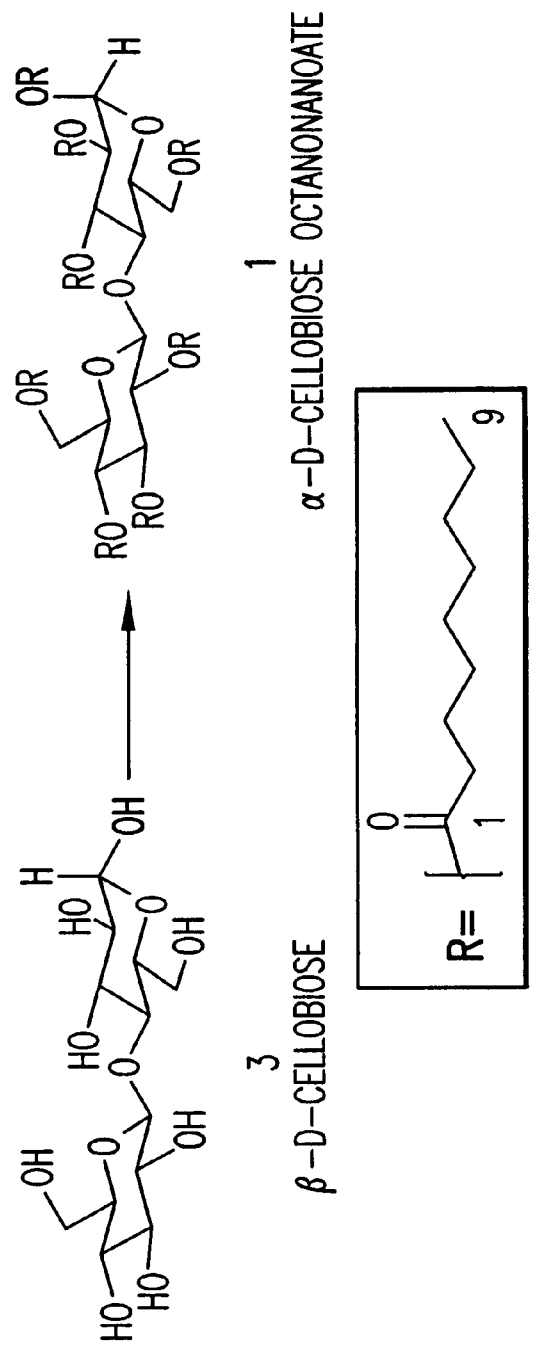
FIG. 2 shows the conversion of β-D-cellobiose to α-D-cellobiose octanonanoate.

Without being bound by theory, it is of note that, from a chemical perspective, it is believed that two processes are occurring in the reaction mixture comprising a disaccharide or trisaccharide-containing material, a $C_6$ to $C_{12}$ fatty acid anhydride-containing material and a catalyst. In one aspect of the reaction, the hydroxyl component of the disaccharide or trisaccharide-containing material is being esterified. In another aspect of the reaction, the anomeric hydroxyl group and/or $C_6$ to $C_{12}$ ester group at the reducing end of the disaccharide or trisaccharide-containing material is being anomerized from the beta orientation to the alpha orientation as illustrated with cellobiose in FIG. 2. Notably, in some disaccharide or trisaccharide-containing materials, the hemiacetal hydroxyl may exist predominantly as the beta anomer. With standard esterification methods, the anomeric hydroxyl may not be converted from the original beta orientation to alpha orientation.

For example, in a common esterification method, an alcohol may be treated with an acid chloride and pyridine. The inventors herein have observed that when the cellobiose is treated with nonanoyl chloride such as in the method of Takada et al., almost no anomerization is observed and β-cellobiose octanonanoate is obtained with very high stereoselectivity (>91% by $^1$H NMR). Moreover, without the use of pyridine to maintain a non-acidic reaction medium, treatment of carbohydrates with acid chlorides generally results in cleavage of glycosidic bonds to give glycosyl chlorides as demonstrated by Debenham and coworkers (Debenham, J. S.; Madsen, R.; Roberts, C.; Fraser-Reid, B. *J. Am. Chem. Soc.* 1995, 117, 3302–3303.)

The present invention utilizes a novel chemical approach to accomplish the esterification/anomerization process with excellent yield of high α-content materials. Moreover, in accordance with the methods herein, it was surprisingly found that it was not necessary to use the exotic and expensive TFAA for esterification of disaccharide and trisaccharide materials, such as cellobiose, with long chain fatty acids as is required in the prior art method of Takada et al. Accordingly, in one aspect, the reaction mixture does not comprise TFAA.

According to the process herein, the high alpha content material may be obtained directly from the reaction medium. Of course, it is possible to subject the $C_6$ to $C_{12}$ disaccharide or trisaccharide fatty acid ester to one or more purification steps to further increase the alpha content of the resulting material. However, in contrast to the methods of Takada et al., it has been surprisingly found that it is possible to obtain high alpha content material directly from the reaction mixture.

The present invention further differs from the method of Takada et al. in the amounts of reactants utilized to prepare high alpha content material. That is, while it is possible to obtain high alpha content with the method of Takada et al., substantially more than catalytic amounts (i.e., 24 equivalents) of TFAA is needed to obtain such purity. (See Example 5B infra). When catalytic amounts (1 equivalent) of TFAA are used, the alpha content of the product is only 43%. (See Example 5A infra). In contrast, the present invention allows the use of catalytic amounts of an esterification catalyst to provide high purity alpha content disaccharide or a trisaccharide $C_6$–$C_{12}$ fatty acid ester directly from the reaction mixture.

It should be made clear the difference between an esterification catalyst and an esterification promoter. A catalyst such as methanesulfonic acid is a material that increases the rate of a chemical reaction without itself undergoing any permanent chemical change. Contrast this to the esterification promoter TFAA which undergoes a permanent chemical change during the course of the esterification reaction. Without being bound by theory, it is generally believed that in the course of the esterification process (forming a nonanoate ester for example), a very reactive mixed anhydride $\{CF_3CO_2CO(CH_2)_7CH_3\}$ is formed in situ. The nonanoyl chain may then be activated by the trifluoroacetyl group allowing subsequent transfer of the fatty acid chain to cellobiose. Over the course of the reaction the trifluoroacetic anhydride (TFAA) may be converted to trifluoroacetic acid.

As utilized herein, the $C_6$–$C_{12}$ fatty acid anhydride-containing material can comprise $C_6$–$C_{12}$ fatty acid anhydride, $C_6$–$C_{12}$ fatty acid or a mixture thereof. In one aspect, the $C_6$–$C_{12}$ fatty acid anhydride in the anhydride-containing material may comprise less than about 6 wt. % impurities, wherein such impurities comprise branched chain carboxylic acid or anhydride materials. In yet another aspect, the anhydride-containing material comprises from about 60 wt. % to about 100 wt. % $C_6$–$C_{12}$ fatty acid anhydride and less than about 40 wt. % $C_6$–$C_{12}$ fatty acid.

In a further aspect, the $C_6$–$C_{12}$ fatty acid anhydride-containing material utilized in the esterification/anomerization comprises impurities in an amount that will result in a final product with less than about 15 wt. % branched ester groups. Still further, the $C_6$–$C_{12}$ fatty acid anhydride-containing material utilized in the esterification/anomerization comprises impurities to result in a final product with an amount of less than about 8 wt. % branched ester groups. One of ordinary skill in the art will recognize that in some circumstances it is more economical to utilize reactants that are not of 100% purity. With respect to the $C_6$–$C_{12}$ fatty acid anhydrides utilized herein, as long as the level of branched ester groups in the product is kept to below about 15 wt. % and, still further, below about 8 wt. %, the end product will be acceptable for the intended uses.

In yet a further aspect, the anhydride-containing material comprises a nonanoic anhydride-containing material, thereby providing a disaccharide or trisaccharide $C_9$ fatty acid ester. One of skill in the art will recognize that it can be difficult to obtain pure $C_9$ materials in amounts useable on a commercial scale. Such materials may contain by-products or impurities. Therefore, in accordance with the processes of the present invention, it may be acceptable for the anhydride-containing material to comprise nonanoic acid in addition to nonanoic anhydride without departing from the intended uses of the invention. In one aspect, the nonanoic anhydride in the nonanoic anhydride-containing material comprises less than about 8 wt. % impurities wherein such impurities comprise short or long chain carboxylic acid materials. In yet another aspect, the nonanoic anhydride-containing material comprises from about 60 wt. % to about 100 wt. % nonanoic anhydride and less than about 40 wt. % nonanoic acid.

In yet a further aspect, the amount the anhydride in the reaction mixture may be from about 1.00 to about 3.00 equivalents per hydroxyl group on the disaccharide or trisaccharide-containing material, thereby providing a degree of substitution on the disaccharide or trisaccharide $C_6$ to $C_{12}$ fatty acid ester of at least about 90%. As utilized herein, the number of equivalents is measured by the amount of anhydride in the anhydride-containing material, without regard for any impurities or by-products, such as acid.

With respect to the catalyst utilized in the processes of the present invention, the catalyst may comprise an akyl or aryl sulfonic acid wherein the sulfonic acid may be substituted or unsubstituted. Yet, still further, the catalyst may comprise one or more of: methanesulfonic acid, ethanesulfonic acid, p-toluenesulfonic acid and benzenesulfonic acid. One of ordinary skill in the art will recognize that mixtures of the stated catalyst materials may also be utilized in the invention herein. In a particular aspect, the catalyst comprises methanesulfonic acid.

In further aspects, the catalyst is utilized in catalytic amounts. In a further aspect, the amount of catalyst in the reaction mixture is from at least about 2 mg to less than about 20 mg per gram of anhydride-containing material. Still further, the amount of catalyst in the reaction mixture is from at least about 6 mg to less than about 16 mg per gram of anhydride-containing material. One of ordinary skill in the art will recognize that the amount of catalyst in the reaction can also be measured in ppm.

In the practice of the processes herein, it has been found that it is sometimes useful to subject the disaccharide or trisaccharide $C_6$ to $C_{12}$ fatty acid ester to a color reducing step. Specifically, the color reducing step may comprise contacting the disaccharide or trisaccharide $C_6$ to $C_{12}$ fatty acid ester with carbon in an amount of from about 0.1 to about 20% by weight as measured by total weight of the reaction mixture. One of ordinary skill in the art will recognize that other methods may be utilized to reduce the color of the disaccharide or trisaccharide $C_6$ to $C_{12}$ fatty acid esters including, but not limited to, chromatography, filtration, and bleaching.

When the disaccharide or trisaccharide $C_6$ to $C_{12}$ fatty acid ester is contacted with carbon during the color reducing step, it may be necessary to remove the carbon prior to isolation of the disaccharide or trisaccharide $C_6$ to $C_{12}$ fatty acid ester.

Techniques known to those skilled in the art, such as filtration or centrifuging, can be used to remove the carbon. However, in the practice of the processes herein, it has been found that filtration times to remove the carbon may, in some aspects, be unacceptably long, particularity when the disaccharide is cellobiose and the cellobiose starting material is prepared by acetolysis of cellulose obtained from wood pulp. Such extended filtration times are believed to be due to the presence of impurities in the cellobiose; these impurities may be the result of residual materials in the cellobiose, such hemicellullose. In the event of long filtration times, it has been found that the addition of certain co-solvents may significantly increase the time required to filter the solution. Particular co-solvents may include, but are not limited to, acetone, ethyl acetate, toluene, and methyl ethyl ketone. When cellobiose having impurities is utilized, it has been found that addition of a co-solvent has been found to increase the filtration rate at greater than 25% over the rate seen without the addition of the co-solvent.

In one aspect, the ratio of co-solvent to disaccharide or trisaccharide $C_6$ to $C_{12}$ fatty acid ester is from about 30:70 to about 70:30. Still further, the ratio may be from about 40:60 or about 45:55 or about 55:45 or about 60:40. In further aspects, the filtration is conducted at from about 25° C. to about 75° C. Still further, the filtration may be conducted at from about 30° C. or about 35° C. or about 40° C. or about 45° C. or about 50° C. or about 55° C. The time for filtration may range from about 5 minutes to about 3 hours. The filtration time may also be from about 10, or about 30, or about 50, or about 60, or about 80, or about 100, or about 120, or about 140, or about 160 minutes, where any of the stated values may be used as an upper or lower endpoint as appropriate.

In a further aspect, the disaccharide or trisaccharide $C_6$ to $C_{12}$ fatty acid ester may be isolated from the reaction mixture via precipitation with a precipitation agent at a temperature of from about 0° C. to about 65° C., in particular, between about 15° C. and about 50° C. In further aspects, the precipitation agent may comprise one or more of: methanol, ethanol or isopropanol. One of ordinary skill in the art will recognize that these alcohols may be utilized either in aqueous or non-aqueous form and that mixtures thereof may be utilized without departing from the scope of the invention. In particular aspects, the precipitation agent may be used in an amount of from about 2 to about 6 volumes, or from 2 to about 4 volumes, based upon total volume of the reaction mixture. Still further, the precipitation agent may comprise one or more of: methanol, ethanol or isopropanol, wherein the alcohol contains greater than about 0% to less than about 8% of water. By "total volume of the reaction mixture," it is meant the volume of the reaction mixture at the end of the esterification/anomerization process. Once the initial precipitation of the product is complete, additional water can be added to harden the product and/or force any remaining product out of solution. The actual water content of the alcohol, if any, may be determined by the number of volumes (relative to the volume of the reaction mixture) of the alcohol and the amount of anhydride containing material used in the esterification.

In yet a further aspect, the processes of the present invention may comprise subjecting the $C_6$ to $C_{12}$ disaccharide or trisaccharide $C_6$ to $C_{12}$ fatty acid ester to an acid hydrolysis step after step (b), thereby providing a partially hydrolyzed disaccharide or trisaccharide $C_6$ to $C_{12}$ fatty acid ester. In a further aspect, the partially hydrolyzed disaccharide or trisaccharide $C_6$ to $C_{12}$ fatty acid ester has a D.S. of from about 50% to about 90% or from about 50% to about 85%.

There are occasions when the preparation of mixed esters or substrates may be desirable. Therefore, in a further aspect, the invention involves contacting a disaccharide or trisaccharide, a nonanoic anhydride containing material and one or more different $C_{6-8}$ to $C_{10-12}$ fatty acids or anhydrides, thereby providing a disaccharide or trisaccharide $C_6$ to $C_{12}$ fatty acid mixed ester with a DS of the $C_9$ ester of from about 50% to about 99% and the DS of the non-$C_9$ ester(s) of from about 1 to about 50%.

In the case of mixed esters, a cellobiose nonanoate that contains a smaller amount of decanoic acid esters can be prepared by the addition of decanoic acid to the general process of this invention. Over the course of the reaction, a mixed anhydride may form at the elevated temperature, thus allowing ready esterification with the decanoic species. This is illustrated in the Examples. As noted above, mixed esters of cellobiose nonanoate can be prepared by the addition of a non-$C_9$ acid or non-$C_9$ anhydrides to the nonanoic anhydride/acid solution and cellobiose. In this aspect, a disaccharide or trisaccharide fatty ester is prepared with the DS of the $C_9$ ester is from about 50% to about 99% and the DS of the non-$C_9$ ester is from about 1% to about 50%. One of ordinary skill in the art will recognize that the substitution pattern of the esters may be highly dependent on the amounts, order of addition, steric and electronic natures of acids and anhydrides used. A particular substitution pattern for the cellobiose esters has a DS of $C_9$ esters of at least 4, a further pattern has a DS of $C_9$ esters of at least 6 and a further pattern has a DS of $C_9$ esters of at least 7.

In a further major aspect, the invention provides disaccharide or trisaccharide $C_6$–$C_{12}$ fatty acid esters made according to the above processes. Still further, the invention provides cellobiose $C_6$–$C_{12}$ fatty acid esters made according to the above process.

The invention will now be described in greater detail by reference to the following non-limiting examples.

EXAMPLES

The following examples are put forth so as to provide those of ordinary skill in the art with a complete disclosure and description of how the compositions of matter and methods claimed herein are made and evaluated, and are not intended to limit the scope of what the inventors regard as the invention. Efforts have been made to insure accuracy with respect to numbers (e.g., amounts, temperature, etc.) but some errors and deviations should be accounted for. Unless indicated otherwise, pressure is at or near atmosphere.

Figure 3:
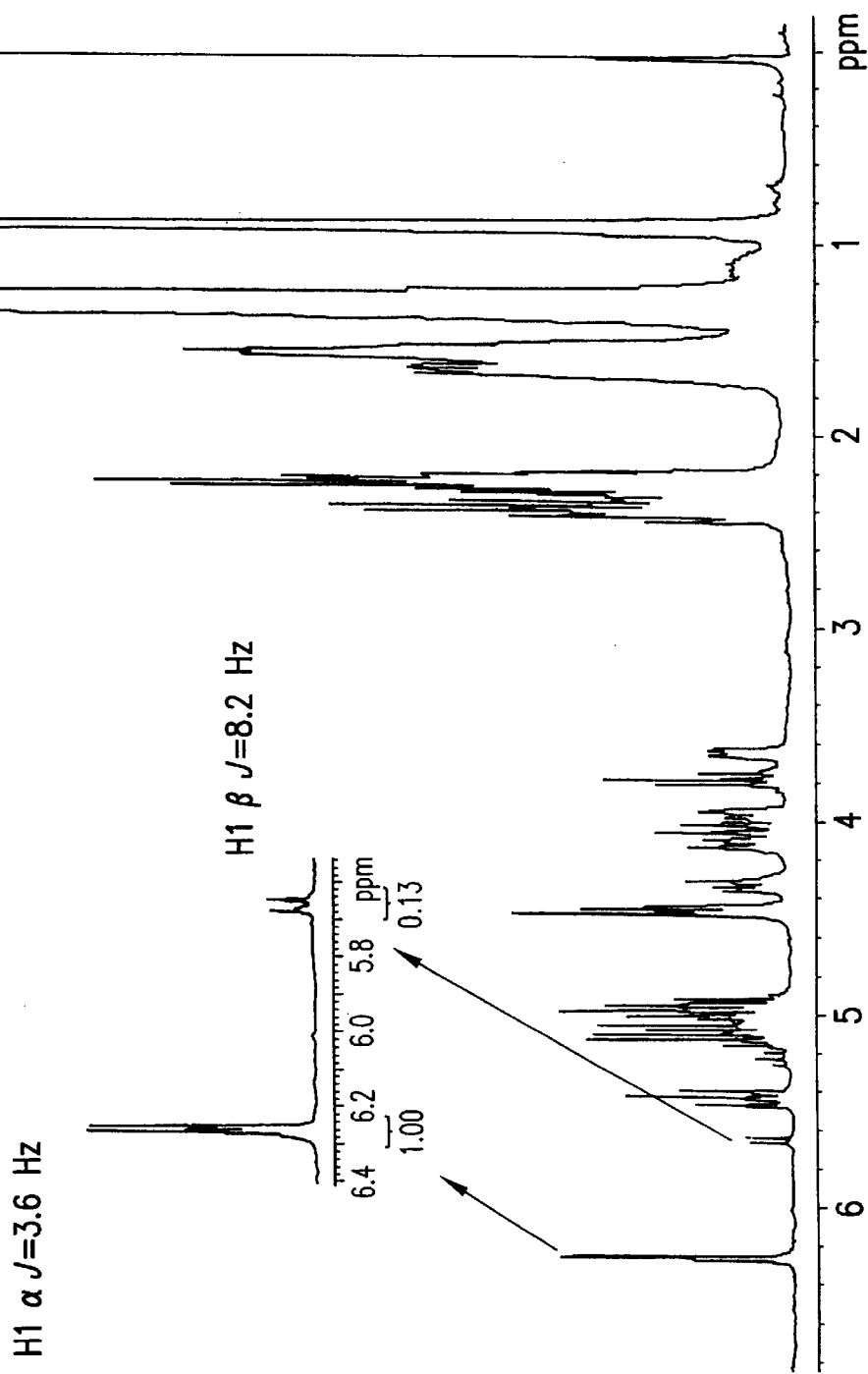
FIG. 3 shows a $^1H$ NMR spectrum of cellobiose octanonanoate with anomeric α and β reducing end ring hydrogens expanded.
Figure 4:
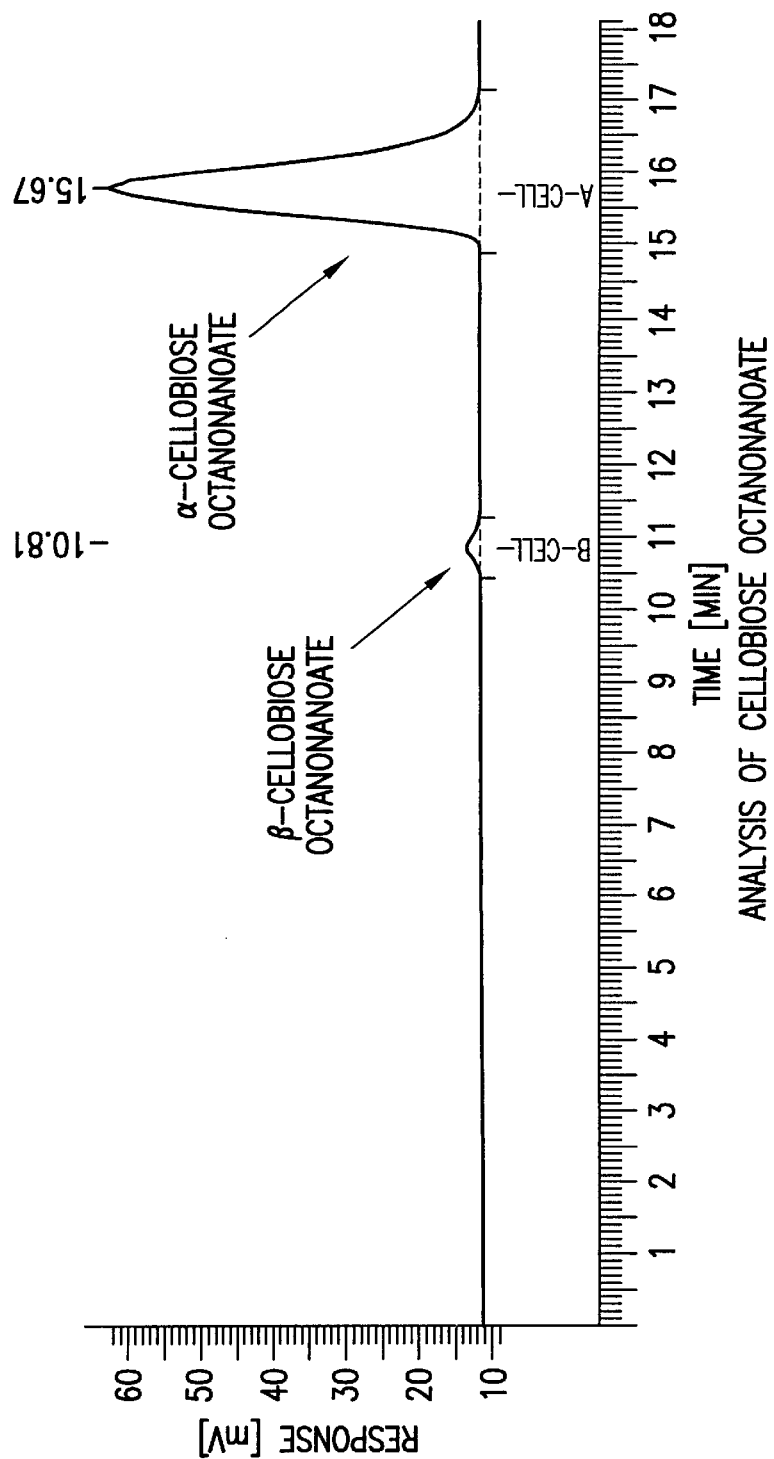
FIG. 4 shows the resolution of the α and β-anomers of cellubiose octanoranoate in an HPLC plot.

In the following examples, $^1H$ and $^{13}C$ NMR (nuclear magnetic resonance) spectroscopy, x-ray fluorescence, EI (electron impact), FD (field desorption) or MALDI (matrix-assisted laser desorption/ionization) mass spectrometry was typically utilized to characterize the products. Nonanoic anhydride weight % was determined by $^1H$ NMR analysis. Anomeric contents were determined either by $^1H$ NMR integration of the anomeric protons (FIG. 3) or by normalized HPLC (high-performance liquid chromatography) weight % (calibrated with pure standards) (FIG. 4). The HPLC method is described in more detail below:

Instrumentation and method conditions: A Hewlett Packard 1100 Liquid Chromatograph with integrated pump and autosampler was used for this work. Detection was done using a Sedex Model 55 Evaporative Light Scattering Detector set at 37° C. and 1.6 bar. Quantification was performed using a Perkin Elmer Turbochrom Clint/Server data acquisition system.

| Chromatographic conditions | |
|---|---|
| Column | Hypersil BDS CN (150 × 4.6 mm), Keystone Scientific-part number 865155-402 |
| Mobile Phase | 0.5% acetic acid, 1.0% THF in hexane |
| Flow | 1.5 mL/min |
| Injection volume | 20 μL |
| Detection | Evaporative Light Scattering |

Standard and sample preparation: Standards and samples were prepared in 1.0% THF in hexane. A stock standard was prepared by dissolving approximately 0.08 g α-D-cellobiose octanonanoate and 0.02 g β-D-cellobiose octanonanoate in 100 ML volumetric flask. Dilutions of 2.5 mL, 5.0 mL, and 7.5 mL to 10.0 mL were done on the stock to give standards ranging in concentration from 200 to 800 ppm for α-D-cellobiose octanonanoate and 50 to 200 ppm for β-D-cellobiose octanonanoate. These levels were chosen for a typical sample that contains approximately 15% β-D-cellobiose octanonanoate and 85% α-D-cellobiose octanonanoate. Samples were prepared at a concentration of approximately 700 ppm (0.07 g to 100 mL).

HPLC could also be used to determine the degree of substitution (DS) when less than fully substituted product was observed (DS 7) as compared to the fully substituted material (DS 8). The method used the following conditions:
Column: Keystone Scientific BDS hypersil C18 (4.6×150 mm)
Flow: 1.2 mL/min
Detection: Refractive Index
Injection volume: 20 μL
Temperature: 40° C.
Mobile Phase: 15/85 THF/MeOH
Sample prep: (in 15/85 THF/MeOH) approximately 100 mg sample to 25 mL The x-ray fluorescence method to determine residual sulfur is described in more detail below:

A Philips PW2400 wavelength dispersive x-ray spectrometer with a chromium target x-ray tube running at 50 kV and 40 mA and helium atmosphere was used for this work. The sample, in the form of a fine powder, is placed in a Somar 24 mm id liquid sample cup with a thin polypropylene window. The sample was placed in the spectrometer and the intensity at the sulfur Ka line as well as the background intensity on both sides of the line was measured using a graphite crystal to resolve the line. The background was averaged and subtracted from the intensity of the emission line. The intensity was converted to concentration using a calibration based on known amounts of sulfuric acid dissolved in 95% ethanol. This should be an overestimate of the actual concentration in the CBON because the higher percent carbon and lower percent oxygen in CBON should result in more efficient transmission of the sulfur x-rays compared to ethanol. The calculated correction factor is 0.85. The actual correction factor could be slightly different because CBON is a loose powder and the calibration used a liquid. The results given were uncorrected. Since uncorrected results were being utilized the method is not completely quantitative, however the reported sulfur values should be very indicative of the relative concentrations of sulfur (which can be equated with residual methanesulfonic acid catalyst) in the samples.

EXAMPLE 1

Preparation of α-Cellobiose Octanonanoate from Cellobiose

The following is a synopsis of a procedure of preparing α-cellobiose octanonanoate from cellobiose according to the inventive methods herein.

Cellobiose (5.00 g, 14.61 mmol), nonanoic anhydride (1.4 equivalents per hydroxyl, 53.14 g at 91.9 weight % (wt %) purity with the balance being nonanoic acid) and methanesulfonic acid (0.744 g, 7.742 mmol) were combined and heated to 77° C. for 12.25 hours. The solution was cooled to room temperature before precipitation in approximately a 2-fold excess of aqueous methanol (7.7 mL $H_2O$ and 120.3 mL methanol). Filtration of the solid and aqueous methanol wash of the cake afforded 20.35 g of material after washing (95% yield). HPLC analysis indicated that the alpha content of the product was 81.6%.

EXAMPLE 2

Preparation of CBON Using a Low Volume Isolation That Also Showed Some Selectivity in the Isolation of the α over the β Anomer Cellobiose (64.29 g, 187.8 mmol), nonanoic anhydride (857.8 g at 73.5 wt % anhydride, with the balance being nonanoic acid) and methanesulfonic acid (12.01 g, 124.97 mmol) were combined and heated to 80° C. for 14 hours. The reaction solution was cooled to 30° C. at which point 33.3% of the solution was used for precipitation studies to find optimal conditions for product isolation. The remaining 66.7% (680 mL) was precipitated in 1360 mL (2 volumes) of aqueous methanol (6% $H_2O$ content). The solid was filtered and washed with aqueous methanol (3% $H_2O$ content). The product was dried in vacuo to afford 175.3 g of CBON (95.6% yield). HPLC analysis indicated that the α-content was 83.5%. Interestingly, an additional 3.66 g (2.0% yield) of CBON could be obtained from the filtrate upon cooling after the methanol rinses had been combined with the initial filtrate. HPLC analysis indicated that the second crop material had a reduced α-content of 66.9%.

This Example demonstrates that the previously discussed Example 1 can be scaled up well with a good α-content being maintained. This Example also demonstrates that the isolation method employed by this invention shows some selectivity for the α-anomer, allowing the β-anomer to remain partly in solution during product precipitation thereby increasing the purity of the isolated product.

EXAMPLE 3

Figure 5:
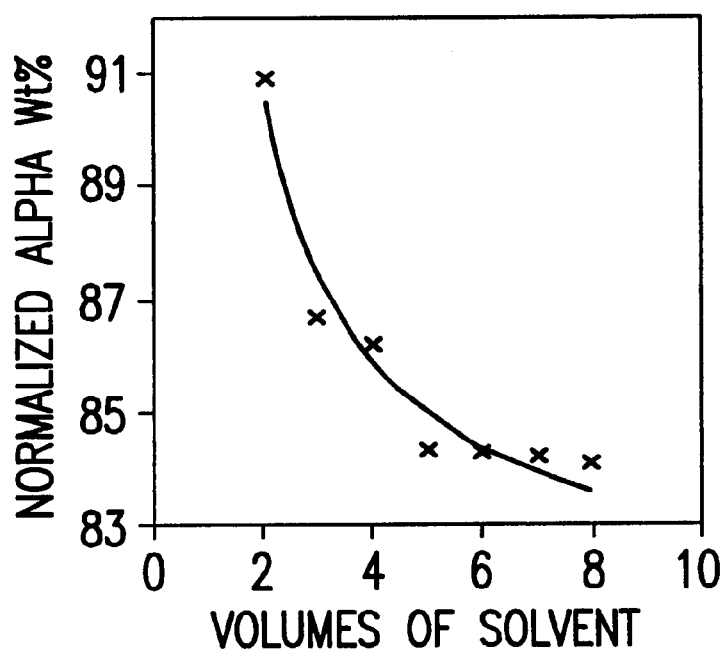
FIG. 5 shows a plot of α-content vs. volumes of precipitation solution.

Precipitation of CBON Using from 8 Volumes to 2 Volumes of Aqueous Methanol and the Effect on α-Content Cellobiose (29.23 g), nonanoic anhydride (373.1 g at 76.5 wt % anhydride with the balance being nonanoic acid) and methanesulfonic acid (5.22 g) were combined and heated to 80° C. for 14.5 h. The solution was cooled to 29° C. before 50 mL portions of the solution were isolated under different conditions. Each 50 mL portion was precipitated in a solution of 96.7% methanol and 3.3% $H_2O$, and the amount of solution was varied from an 8 fold to 2 fold excess of aqueous methanol (400 to 100 mL of isolation solution). The 7 runs account for 77% of the reaction mixture and afforded 86.58 g of product that accounts for an 89% adjusted yield. As can be seen in the following table and graph there is an increase in alpha content in the isolated CBON as the volume of isolation solution is decreased. This trend can be modeled with a 1/x fit with a $R^2$ value of 0.96 a root mean square error of 0.55% alpha (FIG. 5).

TABLE 1

Increase of α-content with decreasing volume of precipitation solution.

| Volumes | α-content by HPLC |
|---------|-------------------|
| 8 | 84.08 |
| 7 | 84.20 |
| 6 | 84.30 |
| 5 | 84.38 |
| 4 | 86.20 |
| 3 | 86.70 |
| 2 | 90.96 |

Normalized alpha Wt % = 81.3139 + 18.4083 Recip(Volumes of solvent)

Summary of Fit

| | |
|---|---|
| RSquare | 0.959701 |
| RSquare Adj | 0.951641 |
| Root Mean Square Error | 0.548838 |
| Mean of Response | 85.83143 |
| Observations (or Sum Wgts) | 7 |

TABLE 1-continued

Increase of α-content with decreasing volume of precipitation solution.

Analysis of Variance

| Source | DF | Sum of Squares | Mean Square | F Ratio |
|---|---|---|---|---|
| Model | 1 | 35.867371 | 35.8674 | 119.0725 |
| Error | 5 | 1.506115 | 0.3012 | Prob > F |
| C Total | 6 | 37.373486 |  | 0.0001 |

Parameter Estimates

| Term | Estimate | Std Error | t Ratio | Prob > \|t\| |
|---|---|---|---|---|
| Intercept | 81.313891 | 0.46306 | 175.60 | <.0001 |
| Recip(Volumes of solvent) | 18.408262 | 1.686969 | 10.91 | 0.0001 |

Where Recip(Volumes of solvent) = 1/(Volumes of solvent)

This Example demonstrates that reducing the volumes of isolation solution while holding the % $H_2O$ constant can allow for the isolation of CBON with a corresponding increase in α-content.

EXAMPLE 4

Application of the Process of the Invention to a Maltose and Lactose

Maltose monohydrate (2.00 g, 5.551 mmol) was combined with nonanoic anhydride (26.26 g, 71.8 wt % anhydride) and MsOH (0.368 g, 3.83 mmol). The reaction was heated to 80° C. for 4.5 hours at which point the reaction was then cooled to room temperature. The material was poured into 8 volumes of aqueous methanol (3.3% $H_2O$ content) where upon the product oiled out of solution. The aqueous methanol was decanted from the liquid product and the oil was washed 3 times with aqueous methanol (0.5% $H_2O$ content). This product was dried in vacuo affording an oil (7.783 g, 96% yield). $^1$H NMR indicated that the alpha content of the product was 76%.

The above reaction was repeated exactly except using lactose monohydrate. Under these conditions the product showed a $^1$H NMR alpha content of 83%.

This Example demonstrates that invention is compatible with oligosaccharides other than cellobiose. It is of interest that the more acid labile glucosel 4 glucose intraglycosidic α-linkage was compatible with the reaction conditions.

EXAMPLE 5a

Comparative Example: Use of TFAA at "Catalytic" Quantities

A 1000 mL 3 neck round bottom flask, equipped with magnetic stirring, reflux condenser, and heating mantle was charged with nonanoic anhydride (143 g, 479 mmol, 1.03 equivalents/OH), TFAA (12.3 g, 58.4 mmol, 1 equivalent) and then cellobiose (20.0 g, 58.4 mmol). The reaction was stirred at 80° C. for 17 hours. Very little of the cellobiose had dissolved into the reaction solution (indicative of very little reaction completion—this was confirmed by thin layer chromatography analysis). The reaction was heated to 100° C. for 6 hours. At this point the reaction mixture was filtered through a medium glass fritted funnel. The light brown solution was poured into 450 mL of methanol in an attempt to precipitate the product. However, no precipitate formed and the product oiled/gelled out of solution. $H_2O$ (32 mL) was added to the MeOH solution and the product was allowed to further oil/gell out of solution. The MeOH solution was decanted away from the oil/gell and the product was washed with aqueous methanol (3% $H_2O$ content). The product was dried at reduced pressure affording cellobiose octanonanoate of low purity (58.88 g impure gel, HPLC assay 62.6% wt % CBON, 36.86 g of actual cellobiose octanonanoate, 43.1% yield). Unreacted cellobiose (10.37 g) was also recovered. HPLC analysis of the product revealed the alpha content to be 41.7%.

TABLE 2a

Contrasts between the TFAA promoter method (used at low quantity) and MsOH catalyst method

|  | TFAA | MsOH |
|---|---|---|
| Product yield | 43.1% | 95.6% |
| α-Content | 41.7% | 83.5% |
| Equivalents of promoter or catalyst | 1 eq. | 0.67 eq. |
| Reaction temperature | 80–100° C. | 80° C. |
| Recovered cellobiose (% of starting material) | 51.9% | 0% |
| Reaction Time (total) | 23 hours | 14 hours |

As can be seen from Table 2a it is not possible to obtain good yield of material using "catalytic" quantities of TFAA instead of another catalyst of the invention, such as methansulfonic acid. Even with 17 hours of reaction time at 80° C. very little reaction occurred. After an additional 6 hours at 100° C., 51.9% of the starting material was still recovered. Moreover, the product had a very low alpha content of 41.7%. Thus when using TFAA in "catalytic" quantities both the esterification and anomerization processes provide low alpha-content cellobiose octanonanoate in poor yield.

EXAMPLE 5b

Comparative Example to the Method of Takeda:
Takada, A.: Ide, N.: Fukuda, T.; Miyamoto, T. *Liq. Crystals* 1995, 19,441–448

A 500 mL 3 neck round bottom flask, equipped with mechanical stirring, reflux condenser, and heating mantle was charged with nonanoic acid (148 g, 935 mmol, 8 equivalents/OH) and TFAA (73.63 g, 350.6 mmol, 3 equivalents/OH). The solution was heated to 100° C. and stirred for 30 min. Cellobiose (5.00 g, 14.61 mmol) was then added to the flask and the reaction was stirred at 100° C. for an additional 6 hours. The reaction was cooled to room temperature and the brown/black liquid was poured into a beaker containing 2,060 mL MeOH and 70 mL $H_2O$. The resulting precipitate was filtered from the liquid and washed 3 times with 100 mL portions of aqueous MeOH (3% $H_2O$/97% MeOH). The solid was dried at reduced pressure affording cellobiose octanonanoate (12.10 g, 56.6% yield). HPLC analysis of the product revealed the alpha content to be 83.9%.

TABLE 2

Contrasts between the TFAA promoter method and MsOH catalyst method (Examples 5 & 2)

|  | TFAA | MsOH |
|---|---|---|
| Product Yield | 56.6% | 95.6% |
| α-Content | 83.9% | 83.5% |
| Equivalents of promoter or catalyst | 24 eq. | 0.67 eq. |
| Reaction Temperature | 100° C. | 80° C. |
| Volumes of aqueous methanol for product isolation | 10 volumes | 2 volumes |
| Space-Time Yield | (0.794) g/(L*hr) | (6.20) g/(L*hr) |

As can be seen from Table 2 there are many advantages to using the process of this invention compared to the one described by Takada (Takada, A.; Ide, N.; Fukuda, T.; Miyamoto, T. *Liq. Crystals* 1995, 19, 441–448). The overall yield of the process is greatly improved while giving essentially the same α-content in the directly isolated product. Furthermore only a catalytic amount of MsOH is used to carry out the esterification and anomerization as compared to the large (24 molar equivalent) excess of TFAA. This greatly reduces the waste and safety hazards of the process. As a result of the more efficient isolation protocol, 2 volumes of aqueous methanol instead of 10, we have demonstrated an almost 8 fold increase in through put as illustrated by the space-time yield (6.20 g vs. 0.794 g per reactor liter-hour).

EXAMPLE 6

Recrystallization of Cellobiose Octanonanoate

Cellobiose octanonanoate (10.00 g, 83.2% α-content) was dissolved in 15 mL of THF at room temperature. Methanol (32 mL) was added and the clear solution sat for 30 min at which point a few fine crystals appeared. An additional 1.2 mL of methanol was added to the solution. After an additional hour a sizable amount of crystals had formed. The crystals were filtered from the liquid and dried at reduced pressure affording 6.70 g of cellobiose octanonanoate.

TABLE 3

Comparison of a-contents before and after recrystallization.

| CBON | α-content |
|---|---|
| Starting material | 83.2% |
| Product | 84.6% |

Product Recovery 67%

This Example demonstrates a recrystallization of cellobiose octanonanoate using THF/methanol. Note that even with a low recovery of product the increase in α-content was only marginal. This may explain why the method of Takada required so many crystallizations (minimum of 4) to achieve an α-content of 97% compare Example 5b).

EXAMPLE 7

Preparation of a Cellobiose Mixed Ester

Figure 6:
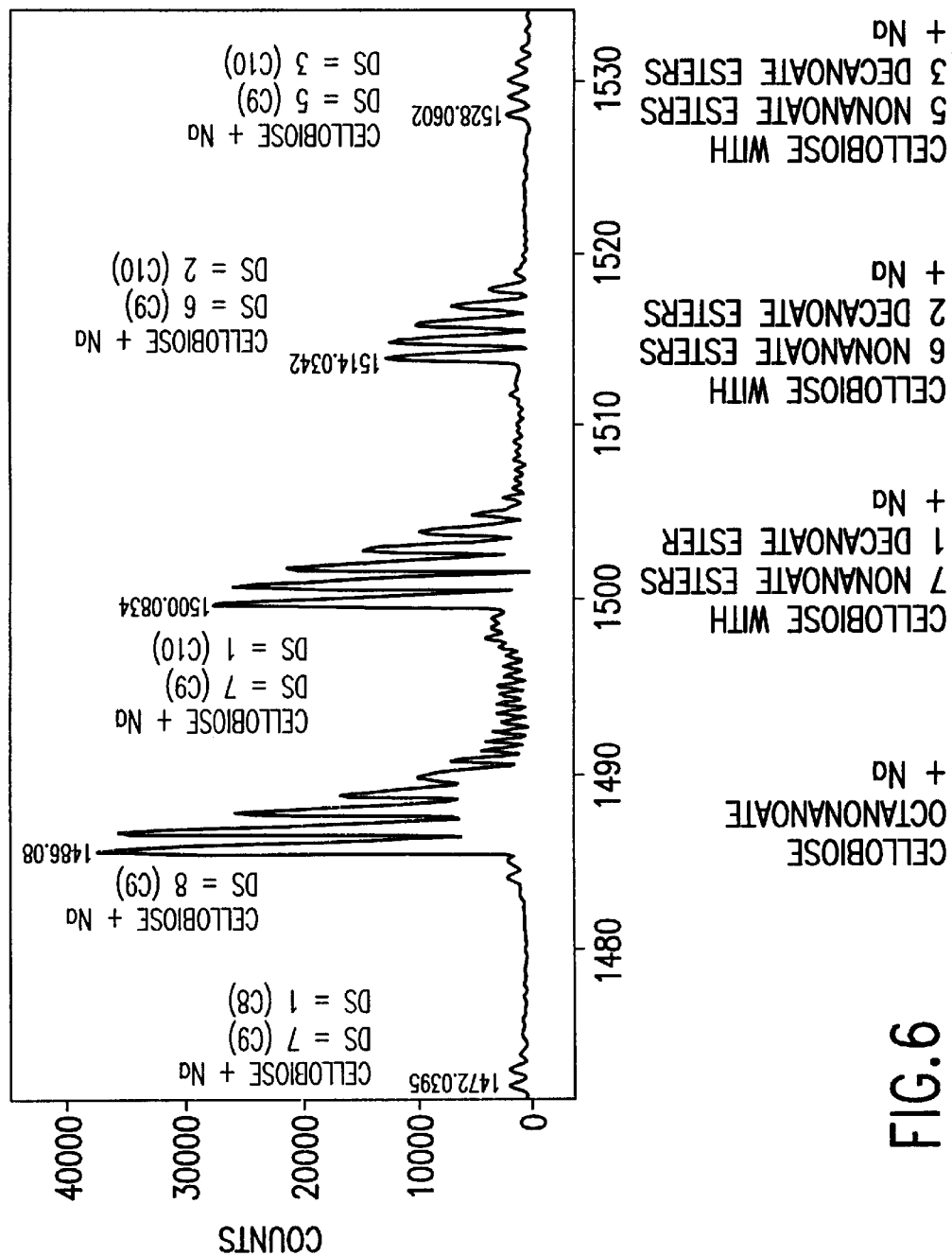
FIG. 6 shows the MALDI spectrum of the nonanoic and decanoic acid mixed cellobiose $C_6$ to $C_{12}$ esters.

Cellobiose (50.00 g, 146.1 mmol), nonanoic anhydride (429 g at 85.4 wt % anhydride, with the balance being nonanoic acid 1.05 eq./OH), decanoic acid (25.16 g, 146.0 mmol) and methanesulfonic acid (6.37 g, 66.29 mmol) were combined and heated to 80° C. for 14.5 hours. Nuchar®SA carbon (12.65 g) was added and the reaction stirred an additional 2 hours. The solution was filtered to remove the carbon and precipitated into methanol (1647 mL) adding 115.3 mL of water to harden the solid. The solid was filtered from the liquids and washed with aqueous methanol (3% $H_2O$ content). The product was dried in vacuo to afford 190.1 g of CBON (89% yield based on a DS of 8 for C9 esters or 88% yield based on a DS of 1 for C10 esters and a DS of 7 for C9 esters). HPLC analysis indicated that the α-content was 84.1%. The presence of the mixed ester product was confirmed by MALDI mass spectrometry (FIG. 6).

This Example demonstrates that it is possible to make mixed esters of cellobiose that have predominantly esters of nonanoic acid. Additionally, carbon treatment of the process liquids was shown to be useful in decolorizing the solution. See Example 12 for further elaboration.

EXAMPLE 8

Preparation of Cellobiose Octanonanoate Using a Minimum Amount of Nonanoic Anhydride with Precipitation into Non-Aqueous Methanol Cellobiose (80.00 g, 233.7 mmol), nonanoic anhydride (686.1 g at 85.4 wt % anhydride, with the balance being nonanoic acid, 1.05 eq. anhydride/OH) and methanesulfonic acid (9.61 g, 100 mmol) were combined and heated to 80° C. for 15 hours. The reaction solution was precipitated in 2274 mL (3 volumes) of methanol. Water (159 mL) was added to harden the solid. The solid was filtered and washed with aqueous methanol (3% $H_2O$ content). The product was dried in vacuo to afford 309.4 g of CBON (90.4% yield). HPLC analysis indicated that the α-content was 82.8%.

This Example demonstrates that as little as one equivalent of anhydride can be used to prepare cellobiose octanonanoate according to the methods of the invention. Additionally, sufficient precipitation of the product can occur in non-aqueous methanol. Water may be added after precipitation to harden the product allowing for more rapid filtration.

EXAMPLE 9

Direct increase in α-Content without Using Recrystallization

Cellobiose (64.29 g, 187.8 mmol), nonanoic anhydride (551.4 g at 85.4 wt % anhydride, with the balance being nonanoic acid) and methanesulfonic acid (7.22 g, 75.13 mmol) were combined and heated to 80° C. for about 17 hours. The reaction solution was cooled, and precipitated in 2034 mL of methanol adding an additional 142 mL of water to harden the resultant solids. The solid was filtered to remove excess liquids and not washed at all. The product was dried in vacuo (18–20" Hg) at 37° C. to afford 406.6 g of material after about 24 hours. At about 48 hours the mass was down to 352.6 g and the solids were dissolved in acetone (650 mL) and decolorized with Nuchar®SA carbon (8.81 g) at 60° C. for 2 hours. The solution was filtered to remove the carbon and the product was precipitated into 2275 mL of aqueous methanol (1% water content). The solid was isolated by filtration and the product was washed with aqueous methanol (3% water content). The product was dried in vacuo to afford 241.7 g of CBON (87.9% yield). The HPLC analysis indicated that the a-content was 87.36%.

This Example demonstrates that it is possible to increase the α-content of the product following the reaction without recrystallization. Typical α-contents following a process of this invention often falls within 82–83.5%. However when the product is isolated and then dried at elevated temperature in the presence of residual catalyst and nonanoic acid (conditions that would occur when the solid product is not washed after isolation) the α-content increases significantly. This is an unexpected result since extended reaction times do not show similar increases in α-content. That this effect is not an artifact of isolating the product twice by precipitation is demonstrated in the following example (Example 10). Carbon treatment as described herein provides a convenient way to help decolorize the product before final isolation.

EXAMPLE 10

Direct Increase in α-Content Without Using Recrystallization as the Unpurified Product Cellobiose (64.29 g, 187.8 mmol), nonanoic anhydride (614.3 g at 87.6 wt % anhydride, with the balance being nonanoic acid) and methanesulfonic acid (8.60 g, 89.49 mmol) were combined and heated to 80° C. for 14 hours. The reaction solution was cooled, and a 235 mL portion of the process liquid was precipitated in 752 mL of methanol adding an additional 60 mL of water to harden the resultant solids. The solid was filtered to remove excess liquids and a portion was set aside for drying. The remaining solid was washed once with a 300 mL portion of aqueous methanol (3% water content) and a sample was set aside for drying. The wash step was repeated on the bulk sample a second and third time as above. On the third wash another sample was removed for drying. A fourth wash and a fifth wash was then completed as above. The remainder of the solid was then dried (in like fashion to the other samples) in vacuo (18–20" Hg) at 37° C. for 24 hours. Each sample was analyzed by HPLC for alpha content and then titrated with base to determine the residual free nonanoic acid content. The samples were also measured by x-ray fluorescence to determine residual sulfur levels that would be indicative of residual catalyst.

TABLE 4

Changes in α-content upon drying at elevated temperature in the presence of decreasing levels of nonanoic and methanesulfonic acid levels.

| Methanol Washes | Alpha Content (%) | Free nonanoic acid (%) | Residual catalyst (ppm) |
|---|---|---|---|
| 0 | 87.2 | 20.1 | 3000 |
| 1 | 84.5 | 9.4 | 878 |
| 3 | 82.6 | 2.0 | 189 |
| 5 | 81.5 | 0.3 | 74 |

This Example demonstrates that the increase in α-content observed when the product is dried in the presence of residual catalyst and nonanoic acid is not an artifact of isolating the product twice by precipitation, since the product has only been through one precipitation.

This Example also demonstrates that additional increases in α-content can be obtained directly without the need for recrystallization. When residual nonanoic acid and catalyst are left in contact with the product after initial product isolation further anomerization can occur during the course of product drying (18–20" Hg at 37° C. for 24 hours). An increase in α-content from 81.5% to 87.2% was seen when comparing samples that had most of the residuals removed (0.3% nonanoic acid & 74 ppm catalyst remaining) to a sample that had 3000 ppm of catalyst still present and contained 20.1% nonanoic acid. This surprising result was quite unexpected since extended reaction times were not observed to produce similar increases in a α-content.

EXAMPLE 11

Hydrolysis of CBON to Produce Cellobiose Esters with a Degree of Substitution Less Than 8

The procedure of Example 9 above was carried out as noted. After the reaction had stirred for 15 hours at 80° C. a 50 mL portion of the reaction solution was precipitated in 3 volumes of methanol (150 mL) subsequently adding water (10.5 mL) to harden the solid. The product (a control sample) was washed thoroughly with aqueous methanol (3% water content) and then dried in vacuo (18–20" Hg) at 37° C.

At the same time that the above sample was taken another 320 mL portion of the reaction solution was transferred to another vessel and the temperature was lowered to 55° C. Methanol (65 mL) and water (10 mL) was added to the reaction solution and samples (50 mL) were taken after the reaction had stirred for 1, 3, 5, 7 and 24 hours. The samples were isolated, washed and dried as the control sample and then analyzed by BPLC to determine the extent of the hydrolysis. Alpha-content in the samples remained essentially unaffected by the hydrolysis conditions and did not show any trends for changing over time (Average α-content=83.0%).

TABLE 5

Hydrolysis of CBON.

| Hydrolysis Time | Area % DS 7 | Area % DS 8 | DS |
|---|---|---|---|
| Control (no hydrolysis) | 0 | 100 | 8 |
| 1 hour | 1.56 | 98.44 | 7.98 |
| 3 hours | 4.01 | 95.99 | 7.96 |
| 5 hours | 5.54 | 94.46 | 7.94 |
| 7 hours | 6.80 | 93.2 | 7.93 |
| 24 hours | 12.78 | 87.22 | 7.87 |

This Example demonstrates that cellobiose nonanoate esters with a DS of less than 8 are readily obtainable by acid catalyzed hydrolysis. Those skilled in the art will recognize that temperature, solvent and water content among other things can readily control the amount and rate of hydrolysis.

EXAMPLE 12

The Use of Activated Carbon to Decolorize the Fatty Acid Process Liquids

Cellobiose (5.00 g), nonanoic anhydride (54.09 g at a minimum of 85 wt % anhydride with the balance being nonanoic acid) and methanesulfonic acid (0.744 g) were combined and heated to 80° C. for 12 hours. At this point five 10 g portions of the reaction solution were isolated. To each 10 g sample was then added a portion of activated carbon (Nuchar®SA) corresponding to 0.8, 2.5, 5.0 and 10 weight % of the sample. The fifth sample was maintained as a control without any carbon treatment. The solutions were all maintained at 80–84° C. for 2 hours before filtration to remove the carbon. The absorbance of the solutions was measured with out dilution at 40° C. on an HP 8452A diode array spectrophotometer at 342 nm using a Na lamp. The absorbance of the starting anhydride was also measured.

TABLE 6

Quantification of color reduction following activated carbon treatment.

| Sample(wt % carbon treatment) | Absorbance |
|---|---|
| Anhydride (0) | 0.36 |
| Control (0) | 3.52 |
| Reaction (0.8%) | 1.65 |
| Reaction (2.5%) | 1.38 |
| Reaction (5.0%) | 1.02 |
| Reaction (10%) | 0.91 |

This Example demonstrates that there is a significant reduction in color following carbon treatment of the reaction solution.

EXAMPLE 13

Direct Preparation of High Alpha Content CBON Through Extended Reaction Hold Times at Low Temperatures Cellobiose (64.29 g, 187.8 mmol), nonanoic anhydride (460 g), nonanoic acid (96 g) and methanesulfonic acid (7.78 g, 81.0 mmol) were combined and heated to 80 ° C. for 14 hours at which point the reaction cooled to 23° C. Over the course of 15.1 days the alpha content was measured by taking a sample (the size is given in Table 7). The sample was precipitated into 4 volumes of methanol adding $H_2O$ to harden the product (14 mL for 50 mL samples and 137 mL for the last sample). The sample was isolated by filtration, washed with aqueous methanol (containing 3% H20) and then dried at reduced pressure. The total amount of CBON recovered was 239.54 g (87% yield). The results are summarized in Table 7.

TABLE 7

Increase in α-content over time at 23° C.

| Sample Size (mL) | Time (d) | Yield (g) | α-content |
|---|---|---|---|
| 50 | 0.38 | 16.69 | 83.7 |
| 50 | 1.38 | 17.85 | 85.5 |
| 50 | 2.38 | 17.95 | 86.9 |
| 50 | 3.34 | 17.85 | 87.8 |
| 490 | 15.13 | 169.2 | 92.6 |

This Example demonstrates that it is possible to achieve further increases in alpha content once the initial esterification and anomerization has been completed. These further increases of alpha content can occur at low temperature so that the extended reaction hold time does not cause extensive glycosidic cleavage and product decomposition.

EXAMPLE 14

The use of Co-Solvents in the Filtration of Cellobiose Octanonanoate to Remove Carbon Cellobiose (75 g) prepared by deacetylation of cellobiose octaacetate obtained by acetolysis of cellulose from wood pulp, nonanoic anhydride (443 g), nonanoic acid (75 g), and methanesulfonic acid (8.51 g) were combined and heated to 80° C. for 16 hours before 6.9 g of carbon was added to the mixture. The mixture containing the carbon was stirred for 45 minutes at 80° C. at which point the the temperature was reduced to 45° C. Aliquots of 80 mL were removed and 60 mL of a co-solvent was added to each aliquot. Each aliquot was then filtered under vaccum through a bed of 7.5 g of Celite 521 filter aid contained on a 150 mL glass filter. The time required to filter each solution was then determined. For comparison purposes, the time required to filter an aliquot not containing a co-solvent was also determined. The results are summarized in Table 8.

TABLE 8

Time required for filtration to remove carbon after the decoloring step.

| Entry | Solvent | Filtration time (sec) |
|---|---|---|
| 1 (a) | None | 4358 |
| 2 | Acetone | 212 |
| 3 | Ethyl Acetate | 241 |
| 4 | Methyl Ethyl Ketone | 305 |
| 5 | Toluene | 1827 |
| 6 | Hexane | 3293 |

(a) The filtration was stopped after only filtering 40 mL of solution due to the long filtration time.

This example demonstrates that co-solvents such as acetone or ethyl acetate are effective in increasing the rate of filtration to remove the carbon after the decoloring step. Other solvents such as hexane are not as effective in increasing the filtration rate.

The invention has been described in detail with particular reference to aspects thereof, but it will be understood that variations and modifications can be effected without departing from the scope and spirit of the invention.

What is claimed is:

1. A method for preparing a disaccharide or a trisaccharide $C_6$–$C_{12}$ fatty acid ester comprising the steps of:
   a. combining a disaccharide or a trisaccharide, a $C_6$–$C_{12}$ fatty acid anhydride and a catalyst to provide a reaction mixture, wherein the reaction mixture does not comprise trifluoroacetic anhydride (TFAA); and
   b. contacting the reaction mixture for a time and at a temperature sufficient to provide a high α-anomer content dissacharide or trisaccharide $C_6$–$C_{12}$ fatty acid ester material having an a-anomer content of from greater than about 50% to about 100%, wherein the high α-anomer content material is obtained directly from the reaction mixture.

2. The method of claim 1, wherein the α-anomer content of the disaccharide or trisaccharide $C_6$–$C_{12}$ fatty acid ester is from about 75 to about 100%.

3. The method of claim 1, wherein the disaccharide or trisaccharide comprises cellobiose, thereby providing a cellobiose ester.

4. The method of claim 3, wherein the cellobiose ester comprises a $C_8$–$C_{10}$ cellobiose ester.

5. The method of claim 1, further comprising performing a purification or a recrystallization step after step (b) thereby increasing the a-anomer content of the disaccharide or trisaccharide $C_6$–$C_{12}$ fatty acid esters.

6. The method of claim 1, father comprising the step of maintaining the disaccharide or trisaccharide $C_6$–$C_{12}$ fatty acid ester at between about 20° C. to about 60° C. in the presence of sufficient reactant, wherein the reactant comprises catalyst, fatty acid and/or anihydride after step (b) thereby further increasing the cc-anomer content of the disaccharide or trisaccharide $C_6$–$C_{12}$ fatty acid ester.

7. The method of claim 1, wherein the anhydride comprises from about 60 wt. % to about 100 wt. % $C_6$–$C_{12}$ fatty acid anhydride and less than about 40 wt. % $C_6$–$C_{12}$ fatty acid.

8. The method of claim 1, wherein the disaccharide or trisaccharide $C_6$–$C_{12}$ fatty acid ester comprises less than about 15 wt. % branched ester groups.

9. The method of claim 1, wherein the anhydride comprises a nonanoic anhydride thereby providing a disaccharide or trisaccharide $C_9$ fatty acid ester.

10. The method of claim 9, wherein the nonanoic anhydride comprises less than about 8 wt. % impurities wherein the impurities comprise branched chain carboxylic acid or carboxylic acid anhydride.

11. The method of claim 9, wherein the nonanoic anhydride comprises from about 60 wt. % nonanoic anhydride to about 100 wt. % nonanoic anhydride and less than about 40 wt. % nonanoic acid.

12. (previously presented) The method of claim 1, wherein the amount of the anhydride in the reaction mixture is from about 1.00 to about 3.00 equivalents per hydroxyl group based on the amount of disaccharide or trisaccharide, thereby providing a degree of substitution on the disaccharide or trisaccharide $C_6$ to $C_{12}$ fatty acid ester of at least about 90%.

13. The method of claim 1, wherein the catalyst comprises one or more of: methanesulfonic acid, ethanesulfonic acid, p-toluenesulfonic acid and benezenesulfonic acid.

14. The method of claim 1, wherein the amount of catalyst in the reaction mixture is from at least about 2 mg to less than about 20 mg per gram of anhydride.

15. The method of claim 1, farther comprising subjecting the disaccharide or trisaccharide $C_6$ to $C_{12}$ fatty acid ester to a color reducing step.

16. The method of claim 15, wherein the color reducing step comprises contacting the disaccharide or trisaccharide $C_6$ to $C_{12}$ fatty acid ester with carbon in an amount of from about 0.1 to about 20% by weight as measured by total weight of the reaction mixture.

17. The method of claim 16, comprising after the carbon contacting step a farther step of adding a solvent comprising one or more of: acetone, ethyl acetate, toluene or methyl ethyl ketone.

18. The method of claim 1, wherein the disaccharide trisaccharide $C_6$ to $C_{12}$ fatty acid ester is isolated from the reaction mixture via precipitation with a precipitation agent at a temperature of from about 0° C. to about 65° C.

19. The method of claim 18, wherein the precipitation agent comprises one or more of: methanol, ethanol or isopropanol containing greater than about 0% to less than about 8% water content.

20. The method of claim 18, wherein the precipitation agent is used in an amount of from about 2 to about 6 volumes of the total volume of the reaction mixture.

21. The method of claim 1, further comprising subjecting the $C_6$ to $C_{12}$ disaccharide or trisaccharide fatty acid ester to an acid hydrolysis step after step (b) thereby providing a partially hydrolyzed disaccharide or trisaccharide $C_6$ to $C_{12}$ fatty acid ester with a degree of substitution of from about 50% to about 85%.

22. The method of claim 1, further comprising contacting the disaccharide or trisaccharide with one or more non-$C_9$ adds or non-$C_9$ anhydrides along with the $C_9$ anhydride thereby providing a disaccharide or trisaccharide fatty acid mixed ester with the degree of substitution of the $C_9$ ester from about greater than 50% to about 99% and the degree of substitution of the non-$C_9$ ester of about greater than 1% to less than about 50%.

* * * * *

UNITED STATES PATENT AND TRADEMARK OFFICE
CERTIFICATE OF CORRECTION

PATENT NO. : 6,667,397 B2
DATED : December 23, 2003
INVENTOR(S) : Debenham et al.

It is certified that error appears in the above-identified patent and that said Letters Patent is hereby corrected as shown below:

Column 18,
Line 28, replace the word "a-anomer" with -- α-anomer --
Line 30, replace the word "father" with -- further --
Line 35, replace the word "cc-anomer" with -- α-anomer --
Line 55, delete the phrase "(previously presented)"

Column 19,
Line 1, replace the word "father" with -- further --

Signed and Sealed this

Thirteenth Day of April, 2004

JON W. DUDAS
*Acting Director of the United States Patent and Trademark Office*